United States Patent
Vetanze

(10) Patent No.: US 7,503,927 B1
(45) Date of Patent: Mar. 17, 2009

(54) MULTIPLE THERAPY SYSTEM AND METHOD

(76) Inventor: Nelson W. Vetanze, 4090 S. Parker Rd., STE 125, Aurora, CO (US) 80014

( * ) Notice: Subject to any disclaimer, the term of this patent is extended or adjusted under 35 U.S.C. 154(b) by 570 days.

(21) Appl. No.: 10/879,251

(22) Filed: Jun. 29, 2004

Related U.S. Application Data

(60) Provisional application No. 60/483,581, filed on Jun. 30, 2003, now abandoned.

(51) Int. Cl.
*A61N 5/06* (2006.01)
(52) U.S. Cl. .................. 607/91; 607/115; 607/152; 607/88
(58) Field of Classification Search .............. 607/1, 607/2, 3
See application file for complete search history.

(56) References Cited

U.S. PATENT DOCUMENTS

| | | | |
|---|---|---|---|
| 4,112,923 A | 9/1978 | Tomecek | |
| 4,233,986 A | 11/1980 | Tannenbaum | |
| 4,535,784 A * | 8/1985 | Rohlicek et al. | 600/548 |
| 4,989,605 A * | 2/1991 | Rossen | 607/46 |
| 5,304,207 A * | 4/1994 | Stromer | 607/3 |
| 5,358,503 A * | 10/1994 | Bertwell et al. | 606/27 |
| 5,385,503 A | 1/1995 | Stouffer et al. | |
| 5,415,617 A | 5/1995 | Kraus | |
| 5,453,074 A | 9/1995 | Imoto | |
| 5,616,140 A * | 4/1997 | Prescott | 606/10 |
| 6,019,482 A | 2/2000 | Everett | |
| 6,094,599 A * | 7/2000 | Bingham et al. | 607/149 |
| 6,187,029 B1 | 2/2001 | Shapiro et al. | |
| 6,221,095 B1 * | 4/2001 | Van Zuylen et al. | 607/88 |
| 6,261,221 B1 | 7/2001 | Tepper et al. | |
| 6,443,978 B1 * | 9/2002 | Zharov | 607/91 |
| 6,860,896 B2 * | 3/2005 | Leber et al. | 607/1 |
| 2002/0143373 A1 * | 10/2002 | Courtnage et al. | 607/91 |
| 2003/0130709 A1 * | 7/2003 | D.C. et al. | 607/88 |
| 2004/0044384 A1 * | 3/2004 | Leber et al. | 607/88 |
| 2005/0042267 A1 * | 2/2005 | Purcell | 424/448 |

* cited by examiner

*Primary Examiner*—Carl H. Layno
*Assistant Examiner*—Jon-Eric C. Morales
(74) *Attorney, Agent, or Firm*—Ramon L. Pizarro; Edwin H. Crabtree

(57) ABSTRACT

A system that provides multiple therapies to a given area of the body of an animal, the system includes a pad for use against the area of the body. The system includes at least one light source, at least one electrical impulse source, and a control module for controlling the frequency of light emitted from the light source and the frequency of the electrical impulses created by the electrical impulse source. The light source provides light-therapy to areas of the body under the pad.

2 Claims, 4 Drawing Sheets

MULTIPLE THERAPY SYSTEM AND METHOD

REFERENCE TO RELATED APPLICATIONS

This application claims the benefit of my provisional application having Ser. No. 60/483,581, filed Jun. 30, 2003, now abandoned.

BACKGROUND OF THE INVENTION (a) Field of the Invention

This invention generally relates to a device or system for applying several types of therapies to an area of the body. More particularly, but not by way of limitation, to a system that provides a combination of therapies at one time, the therapies including combinations of light, pulsed electromagnetic, electrical impulse, and vibratory massage.

(b) Discussion of Known Art

Therapies such as light therapy, pulsed electromagnetic, electrical impulse, and vibratory massage, have long been recognized as effective for treatment of muscular and joint pain. A significant problem associated with these therapies, however, is that the body becomes adapted to the stimulus, causing the therapies to become less effective.

One approach at addressing the problem of adaptation to the therapy has been to vary duration of the impulses provided by each of the diodes or light sources. Accordingly, U.S. Pat. No. 6,187,029 to Shapiro et al teaches the variation of the wavelength of light and the frequency of pulsation of the various diodes or light sources. Additionally, Shapiro teaches the use of heat in combination with the varying light pulses to treat and reduce the problem of adaptation.

SUMMARY

It has been discovered that the problems left unanswered by known art can be solved by providing a system that provides multiple therapies to a given area of the body of an animal, the system includes a pad for use against the area of the body, which includes:

At least one light source;

At least one electrical impulse source; and

A control module for controlling the frequency of light emitted from the light source and the frequency of the electrical impulses created by the electrical impulse source. The light source provides light-therapy to areas of the body under the pad.

According to one example of the invention several light sources and several electrical impulse sources are intermixed on a pad. The pad is designed to be placed over the area to be treated, and may be flexible to allow the pad to conform to the contours of the person or animal being treated. Alternatively, the pad may be of a rigid shape that allows the device to be pressed against the area being treated, causing the person or animal's body to deform around the pad to allow the electrical impulse sources and light sources to contact or come in close proximity with the tissue being treated.

According to another example of the invention, the pad includes light sources, electrical impulse sources or contacts, and vibration sources or magnetic flux sources. It is further contemplated that the device may also include all four therapy devices. That is the pad may include light sources, electrical impulse sources or contacts, vibration sources, and magnetic flux sources.

It is further contemplated that the individual sources of therapies may be independently controlled. With such an arrangement the person administering the treatment may control the intensity and manner in which the treatments are applied. For instance, it is contemplated that application of the different therapies may be random in terms of both source of therapy, duration of pulse or application, and frequency of application. Thus, for example, each of the light sources may be activated at varying intensities, for different lengths of time, with different light sources on the surface of the pad being activated at different times. This variation would appear random to the tissue being treated, and thus minimizing the possibility of adaptation.

Similarly, it is contemplated that the electrical impulse sources may be activated in a similar fashion. This means that the user may select variations in the intensity, frequency of activation of each source or contact, and order or randomness of activation of each of the contacts. It is contemplated that a similar method of activation may be carried out with the application of magnetic resonance, but it has been found that the body is not likely to adapt to the application of a magnetic flux, and thus it is contemplated that the magnetic flux may be applied in a constant manner over the entire area being treated. The application of heat may also be varied as discussed with light sources, but it has also been found that heat may be effectively applied in an alternating manner, with heat and cold or heat and no heating being applied.

It has been found that the simultaneous application of several of these therapies at once is particularly effective. Thus, it is contemplated that the pad may include several alternating light sources and several alternating electrical impulse sources.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
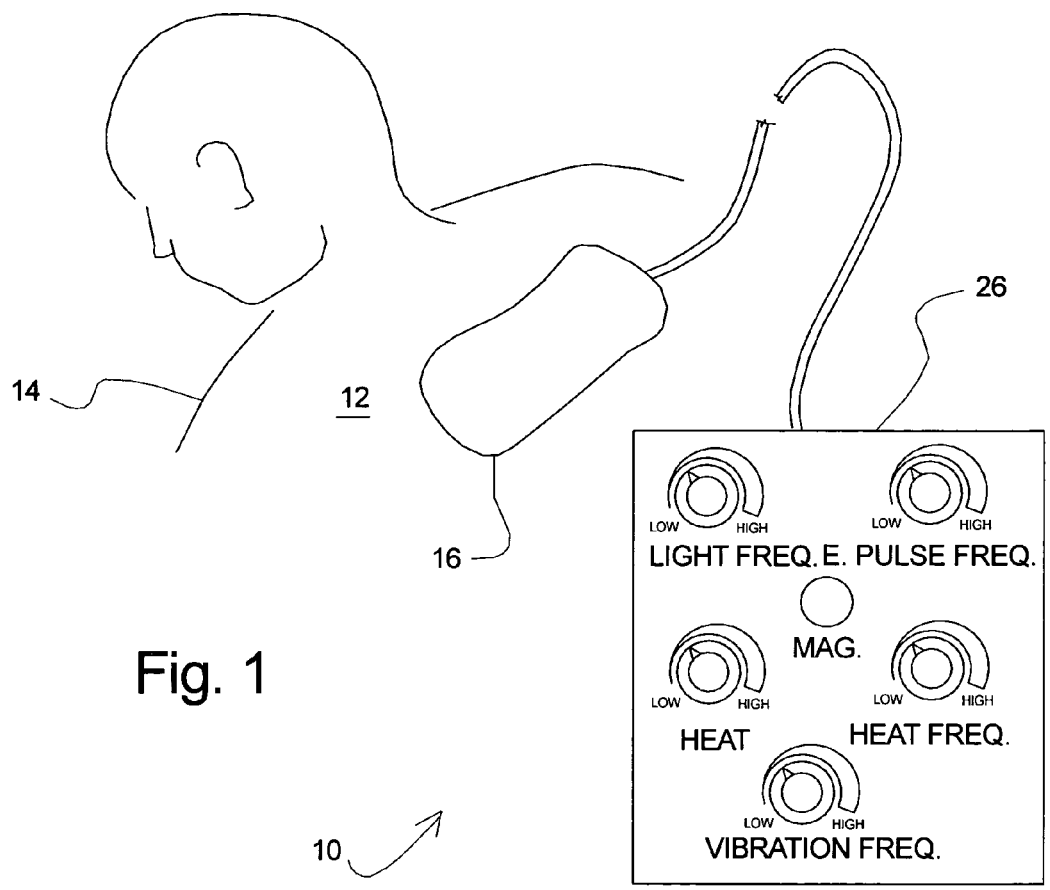
FIG. 1 illustrates the invention in use.
Figure 2:
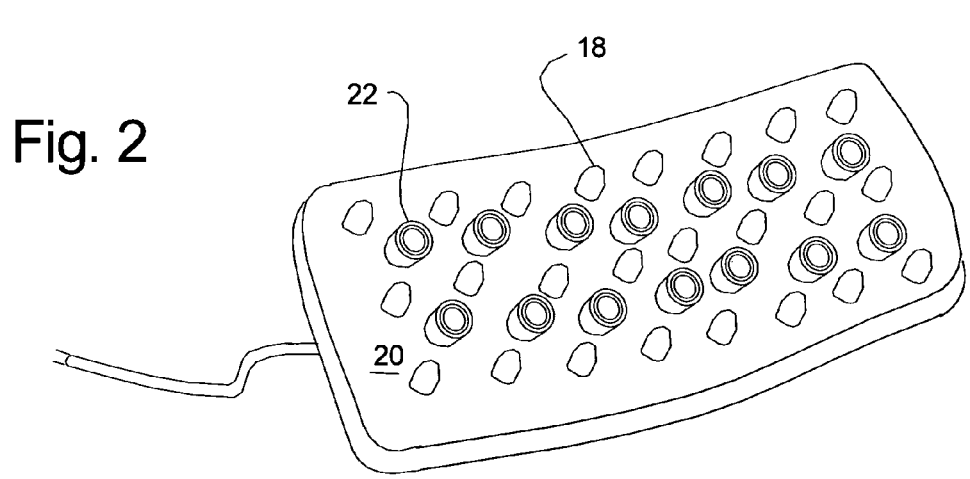
FIG. 2 illustrates an example of the placement of the various lights and electrical pulse components on the pad.

Turning now to FIGS. 1 and 2 where a system 10 for providing multiple therapies to an area 12 of the body of an organism, such as a person 14. It is contemplated that the system 10 will include a pad 16 that has been adapted for use against the area 12 of the body. The adaptation for use on the area of the body may include formed curvatures or flexible features, such as a flexible base. It is further contemplated that the pad 16 will include at least one light source 18. It is contemplated that the light source 18 will include LED's (light emitting diodes) that are mounted on a surface 20 of the pad 16.

Additionally, it is contemplated that at least one electrical impulse source 22 will also be mounted from the pad 16. Each of the electrical impulse sources 22 will provide a low power electrical impulse to the area being treated. Accordingly, the each of the electrical impulse sources 22 will include contacts 24 that will be used to contact the skin and transmit these impulses to the area being treated.

Still further, it is contemplated that a control module 26 will be used in conjunction with the pad 16. The control module 26 may be mounted directly on the pad 16 may be a separate, remote unit, as illustrated in FIG. 2. The control module 26 will include circuitry for controlling the frequency and/or intensity of the light emitted from the light sources 18. The circuitry used for the delivering and controlling the power to the light sources 18 may include transistor based systems, programmed systems, or simply switch based systems that control the pulsing of the LEDs. As shown on FIG. 1, it is contemplated that the control module 26 will provide controls 28 that will allow the therapist to adjust the light pulse frequency. It is important to note that the frequency of the light being emitted by the LED is defined by the particular LED being used. Thus it is contemplated that, in the event that a light source that can vary the frequency of the light cannot be obtained, various LEDs or other light sources each which provides light of a desired frequency may be used.

The control module 26 will also include a system for randomly (or seemingly randomly) activating each of the light sources 18. This varied activation will greatly reduce the body's ability to adapt to the presence of the light. Additionally, the variation of the activation will result in the variation of the light impulse and light frequency. The duration of each impulse may also be varied.

It is further contemplated that the frequency (meaning the number of pulses during a given period of time) of the electrical impulses created by the electrical impulse sources 22, as well as the intensity of the electrical pulse delivered may also be varied with the disclosed invention.

Figure 3:
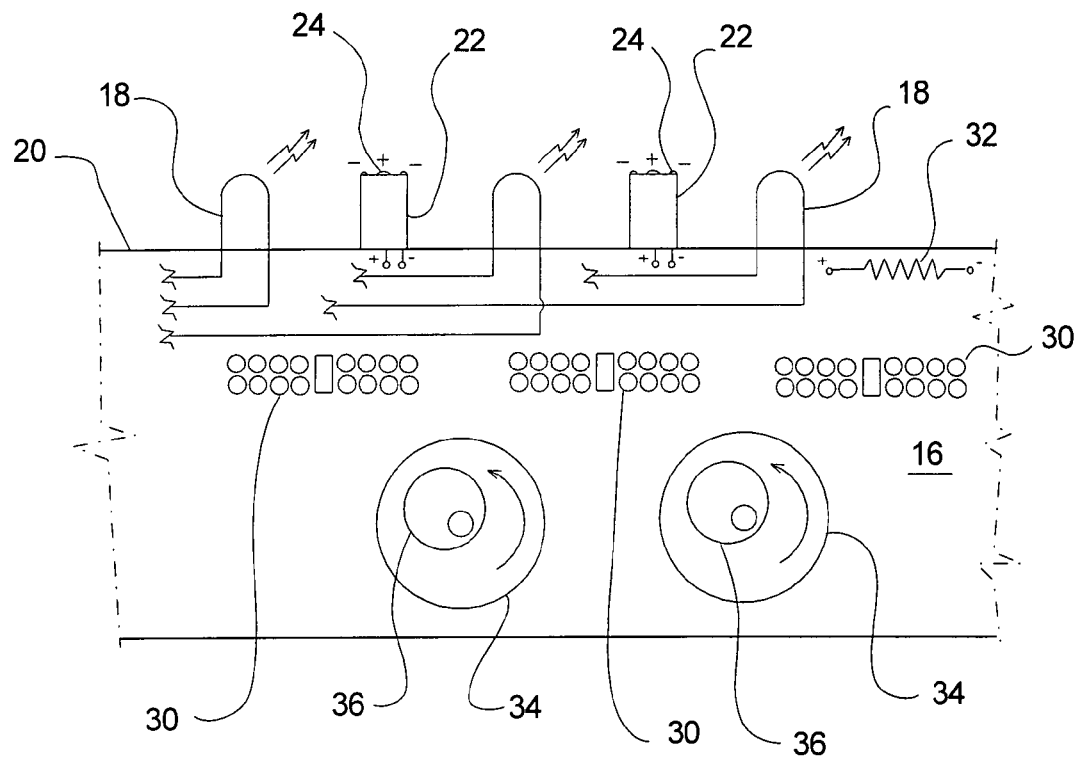
FIG. 3 is a sectional view taken from FIG. 2, illustrating several therapy devices imbedded in the pad.
Figure 4:
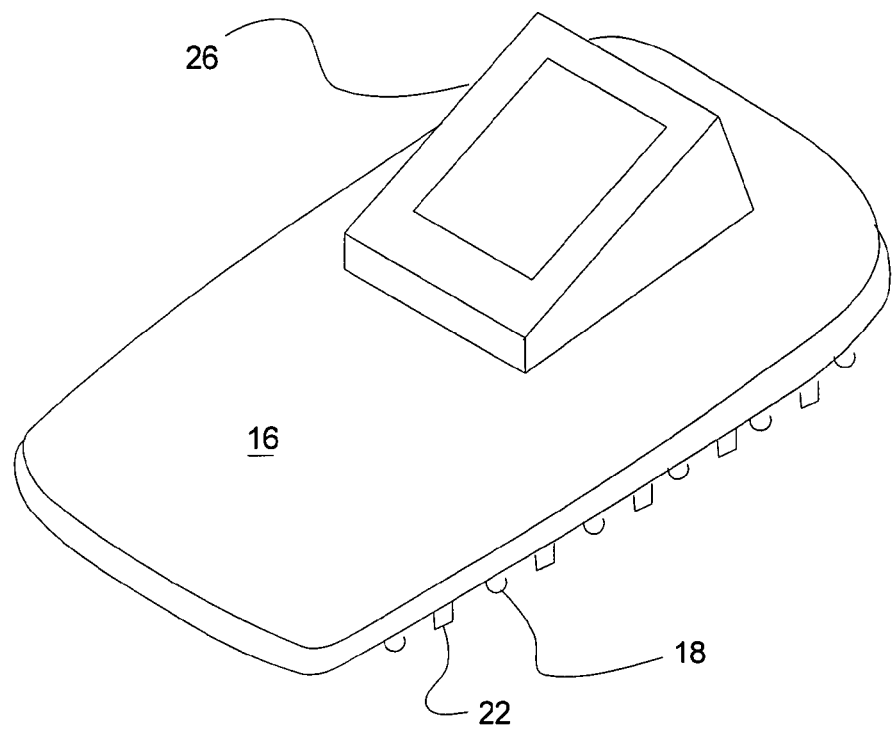
FIG. 4 is an example of a self contained multi-therapy device.

Turning now to FIG. 3, it will be understood that it is contemplated that the pad 16 may also include electromagnets 30, which will produce a magnetic field that is projected into the tissue being treated.

Also illustrated in FIG. 3 is the inclusion of a heat source 32, which may be an electrical resistor or fluid based heating system. The advantage of a fluid based heating system, which would use flexible ducts that carry a working fluid throughout the pad 16 is that the temperature of the fluid may be varied. Thus the pad 16 may be used to provide heating as well as cooling of the area being treated.

Still further, FIG. 3 illustrates that at least one vibrator 34, such as the rotating offset weight 36 vibrator shown in FIG. 3 may also be incorporated into the pad. The vibration providing the benefits of known muscle relaxation therapy caused by the vibration. It is contemplated that the intensity of the vibration may also be controlled through the control module 26.

It has been discovered that providing multiple therapies, such as light, electrical impulse, heat, magnetism, vibration, and the like through a single delivery system, such as the pad 16 produces unexpected, synergistic beneficial results in the treatment of tissue or joint ailments. In clinical experiments conducted by the inventor, approximately one hundred and fifty patients whose soft tissue symptoms (stain, sprain, myofacitis, muscle spasm, arthritis, carpal tunnel, and segmental dysfunction) ranged from acute to chronic, also moderate to severe, were treated using light, electrical pulse, impulse and vibratory massage from a single delivery system resulted in noticeable relief of symptoms ranging from moderate to complete alleviation of symptoms. The results were confirmed using Surface EMG and Computer Range of Motion techniques, which indicated reduction in spasm and an increase in range of motion in all tested subjects. The inventor's observations of results of individual application of the therapies indicated that that the simultaneous application of several of these therapies yielded better results than the application of a single therapy at a time to the afflicted tissue. Thus, it will be appreciated that the disclosed system not only solves issues of adaptation, but also provides new and useful, synergistic therapeutic results.

Figure 5:
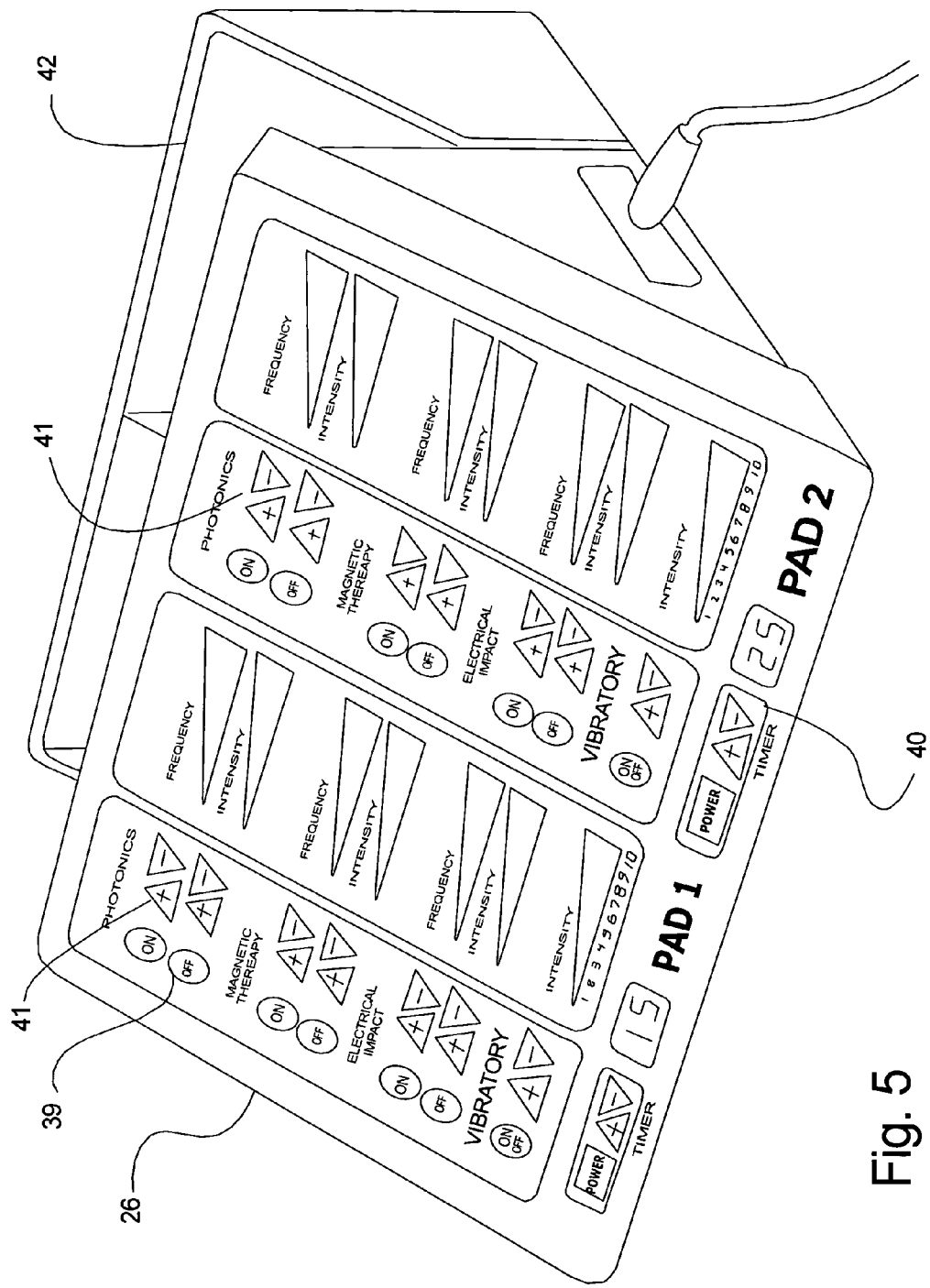
FIG. 5 is an example of a control module used to control the pad, and is designed to allow the use of more than one pad at a time.

Turning to FIG. 5 where another example of a control module 26 used to control the pad 16. As illustrated, the control module 26 includes individual on/off switches 39 and intensity level controls 41 of the photonic (light source 18) therapy, the magnetic therapy (control of the electromagnets 30), electrical impact (electrical impulse sources 22), and vibration (controls the vibrators 34). Control of an independent heat source is not shown, but it is contemplated that the light sources 18 will provide heat, and thus the example shown in FIG. 5 allows control of heat therapy through the control of the light sources 18.

Additionally, the control module 26 illustrated in FIG. 5, allows control of the intensity at which these therapies are administered, as well as a timer 40 that allows the precise control of the length of time that the therapies are administered. FIG. 5 also shows that the control module 26 can control more than one pad 16, so that therapies may be administered to more than one patient or to one patient at more than one location on the body. The control module 26 is also shown as having storage trays 42 that allow storage of the pads 16 with the control modules.

Figure 6:
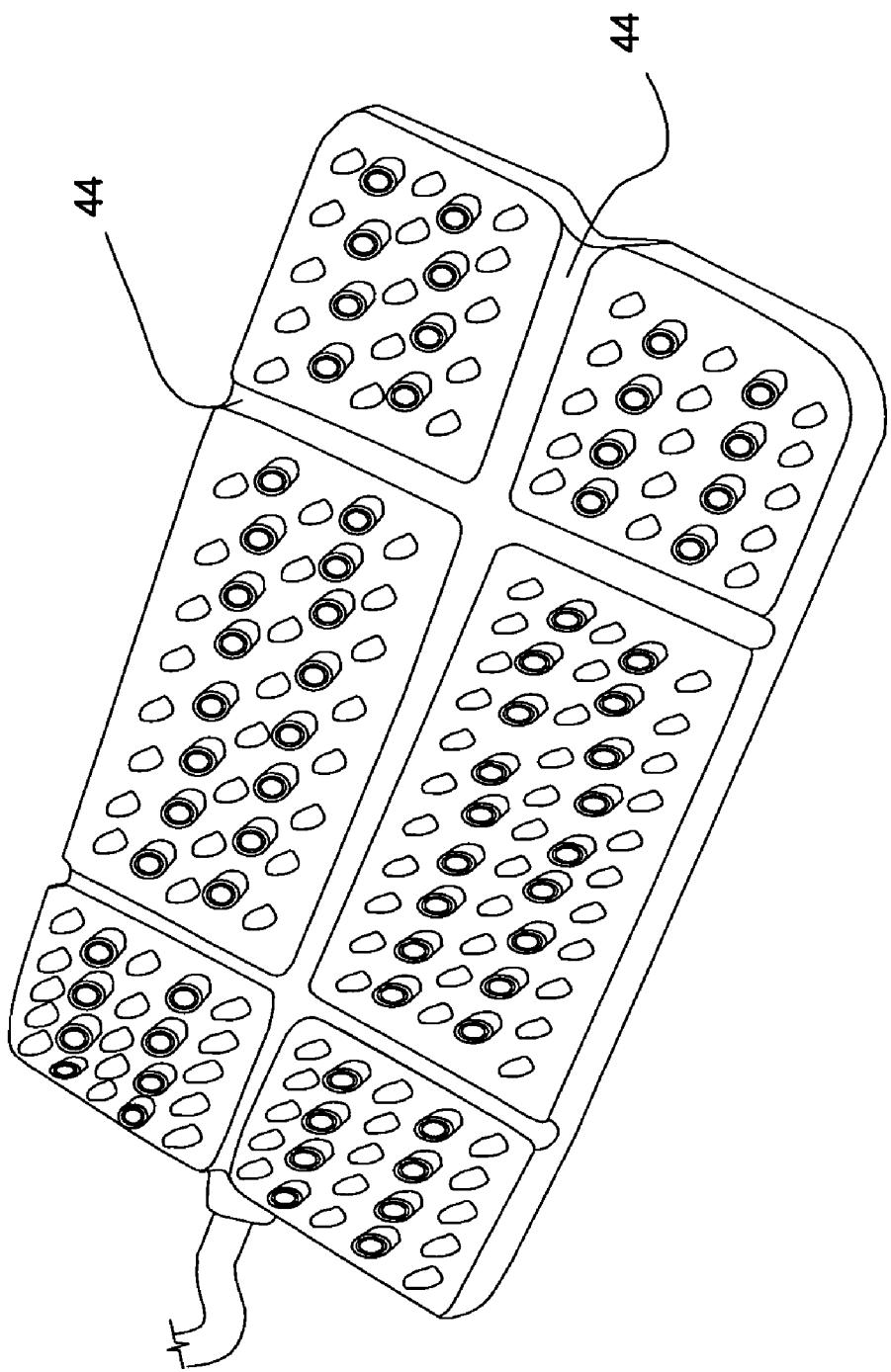
FIG. 6 illustrates an example of a flexible pad. The pad including recessed areas that provide flexibility to the pad to allow the pad to better conform to contours of the body.

Turning to FIG. 6 it will be understood that it is contemplated that the pad may include recessed areas 44, which are merely grooved or weakened areas that provide flexibility to the pad 16. These recessed areas 44 allow the pad 16 to better conform to contours of the body.

Thus it can be appreciated that the above-described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A method for providing therapy to an area of an organism having a musco-skeletal system, the method comprising:

selecting an area over the musco-skeletal system to be treated;

providing a flexible pad containing weakened areas, the weakened areas comprising intersecting grooves that extend along and into the pad at right angles to one another, but not through the pad, the grooves being deep enough to provide flexibility to the pad along the grooves in order to provide flexibility to the pad about at least two axis, and a plurality of light sources and a plurality of electrodes mounted on the flexible pad, several of the light sources and of the electrodes being separated by the grooves;

simultaneously applying to the selected area of the musco-skeletal system:

light from the plurality of light sources in a sufficient amount to produce a therapeutic effect;

electrical impulses from the plurality of electrodes; and delivering the light emitted from the light source and the electrical impulses to the selected area at about the same time, so that the flexible pad conforms to the selected area of the musco-skeletal system, allowing the plurality of electrodes and the plurality of light sources to contact selected area of the musco-skeletal system.

2. A method for providing therapy to an area of an organism having a musco-skeletal system, the method comprising:

selecting an area over the musco-skeletal system to be treated;

providing a flexible pad containing weakened areas on a surface of the pad, the weakened areas comprising intersecting grooves that extend along and into the pad at right angles to one another, but not through the pad, the grooves being deep enough to provide flexibility to the pad along the grooves such in order to provide multi-axial flexibility to the pad, and a plurality of light sources and a plurality of electrodes mounted on the surface of the flexible pad, several of the light sources and of the electrodes being separated by the grooves and being on the same surface as the grooves;

simultaneously applying to the selected area of the musco-skeletal system:

light from the plurality of light sources in a sufficient amount to produce a therapeutic effect;

electrical impulses from the plurality of electrodes; and delivering the light emitted from the light source and the electrical impulses to the selected area at about the same time, so that the flexible pad conforms to the selected area of the musco-skeletal system, allowing the plurality of electrodes and the plurality of light sources to contact selected area of the musco-skeletal system.

* * * * *